United States Patent [19]

Manning

[11] 4,036,781

[45] July 19, 1977

[54] DEHYDROGENATION CATALYST

[75] Inventor: Harold E. Manning, Houston, Tex.

[73] Assignee: Petro-Tex Chemical Corporation, Houston, Tex.

[21] Appl. No.: 593,726

[22] Filed: July 7, 1975

Related U.S. Application Data

[62] Division of Ser. No. 515,328, Oct. 16, 1974, abandoned.

[51] Int. Cl.$^2$ .................. B01J 21/04; B01J 21/10; B01J 23/26; B01J 27/02
[52] U.S. Cl. ............................................ 252/439
[58] Field of Search .............. 252/432, 439, 455 R, 252/457, 465, 468; 106/59; 423/596

[56] References Cited

U.S. PATENT DOCUMENTS

| | | | |
|---|---|---|---|
| 2,161,984 | 6/1939 | Sweeney et al. | 260/683.3 |
| 2,205,141 | 6/1940 | Heard | 260/683.3 |
| 3,361,584 | 1/1968 | Mayberry | 106/59 |
| 3,801,672 | 4/1974 | Bajars | 260/680 E |

OTHER PUBLICATIONS

"Chromites", Kirk-Othmer, Encyclopedia of Chemical Technology, 2nd ed., vol. 5 (1964), p. 496.

*Primary Examiner*—W. J. Shine
*Attorney, Agent, or Firm*—Kenneth H. Johnson; N. Elton Dry

[57] ABSTRACT

Magnesium chromites promoted with B, Si, Sn, Pb and Se have been found to be superior to chromia-alumina type dehydrogenation catalysts, for example, in the dehydrogenation of n-butane. The promoter is either added to the preformed magnesium chromite or is incorporated into the spinel structure of the chromite itself or added in both ways. The promoter will be present in the catalyst from all sources in a mol ratio of promoter: $MgCr_2O_4$ of 0.001 to 0.25:1. The ratio will more usually be 0.03 to 0.08:1 promoter: $MgCr_2O_4$.

3 Claims, No Drawings

DEHYDROGENATION CATALYST

This application is a Division of Ser. No. 515,328 filed Oct. 16, 1974, and now abandoned.

This invention relates to a process for the dehydrogenation of gaseous hydrocarbons and the catalyst employed. More specifically the process is a cyclic process wherein there are alternating cycles of dehydrogenation and catalyst regeneration.

The process is a cyclic process in which gaseous hydrocarbons such as butane or isopentanes are dehydrogenated over a suitable catalyst to produce butenes and butadiene and isopentene and isoprene respectively. After each dehydrogenation cycle there is a catalyst regeneration cycle in which the accumulated coke is burned off by passing molecular oxygen through the catalyst followed by another dehydrogenation cycle and so on.

The chromia-alumina catalysts have been recognized for a number of years as the most preferred catalyst for this type process. The chromia-alumina catalysts are prepared by treating activated alumina with a solution of chromic acid, draining off the excess acid from the alumina, drying and heat treating at about 1400° F. Commercial chromia-alumina dehydrogenation catalysts normally contain about 20% chromium oxide. Preparative methods are shown, for example in U.S. Pat Nos. 2,399,678 and 2,419,997.

Other chromia-metal oxide materials have been investigated for their dehydrogenation capabilities. One of the more prominent among these has been chromia-magnesia which has been found to be a poor second to chromia-alumina. Several patents were issued to Tropsch in the late 1930's relating to magnesia based chromia dehydrogenation catalysts, e.g., U.S. Pat. Nos. 2,122,786; 2,122,787; 2,122,790; and 2,148,140. Pitzer disclosed chromia-magnesia-alumina dehydrogenation catalyst in U.S. Pat. No. 2,638,455. U.S. Pat. No. 3,781,376 discloses a superior dehydrogenation catalyst of an aluminum promoted magnesium chromite. It is an object of the present invention to find an alternative catalyst to chromia-alumina for use in cyclic dehydrogenation processes. It is another object of the present invention to find a catalyst superior to the chromia-alumina catalysts for use in dehydrogenation. It is still a further object to provide a process which will give better results than presently achieved with chromia-alumina catalysts. It is a particular object to provide improved magnesium chromite catalysts. Other objects and advantages of the present invention will be apparent from the following description.

SUMMARY OF THE INVENTION

Briefly stated, the present invention lies in a dehydrogenation catalyst consisting essentially of magnesium chromite or an aluminum promoted magnesium chromite and a promoting amount of boron, silicon, tin, lead and selenium. A promoting amount may be from 0.001 to 0.25 mol per mol of magnesium chromite or more preferably 0.03 to 0.08 mol per mol of $MgCr_2O_4$. Improvement in the dehydrogenation process employing these promoted catalysts is also an aspect of the present invention.

DESCRIPTION OF THE INVENTION AND PREFERRED EMBODIMENTS

The objects of the present invention have been achieved by use of a novel catalyst containing chromium, magnesium, a promoter selected from the group consisting of boron, silicon, tin, lead, selenium and oxygen. The catalysts may also contain aluminum. The catalysts are characterized as magnesium chromites either in admixture with the promoter or containing the promoter therein. Similarly, the chromites may be in admixture with aluminum oxide or containing aluminum therein. The chromites generally have a spinel structure. This can be attributed to the octahedral site preference energy of $Cr^{3+}$ which is the greatest of all cations which can form spinel-type structures. The crystal structure of the chromites will usually be a face centered cubic form.

The catalysts of the present invention are predominately chromites, that is, they contain more than 50% by weight of the chromite. Preferably the catalysts contain 75% or more chromites, i.e., 90% chromites. The present chromites may be represented by the formula $MgCr_2O_4$.

The aluminum component of the catalyst may also be present as a constituent of the chromite, however, it is necessary that the aluminum be a portion of the chromite and may be present in addition to the metal chromite in the form of aluminum oxide. The aluminum can be incorporated into the chromite by backing out a portion of the chromium. Aluminum can be substituted for up to less than 50% of the chromium atoms of the chromite. Such chromites have the formula $MgAl_xCr_{2-x}O_4$ where x is a number of from more than 0 up to less than 1.

The magnesium chromites of the present invention exhibit a certain type of X-ray diffraction pattern. The peaks observed in the X-ray diffraction pattern may not have sharp peaks such as those found, e.g., in highly crystalline material of the same chemical composition, but can and do frequently exhibit relatively broad reflection peaks. The degree of sharpness of the reflection peak may be measured by the reflection peak band width at half height (W/h/2). In other words, the width of the reflection peak as measured at one-half of the distance to the top of the peak is the "band width at half height". The band width at half height is measured in units of ° 2 theta. Techniques for measuring the band widths are discussed, e.g., in Chapter 9 of Klug and Alexander, X-ray Diffraction Procedures, John Wiley and Son, N.Y., 1954. The observed band widths at half height of the preferred compositions of this invention are at least 0.12° 2 theta and normally will be at least 0.16° 2 theta*. The particular reflection peak used to measure the band width at one-half height is the reflection peak having Miller (hkl) indices of 111. (See, e.g., Chapter of Klug and Alexander, ibid). This description is not to be taken as a limitation of the invention in regard to the relationship between composition activity and band width.

*The powder diffraction may be made, e.g., with a Norelco constant potential diffraction unit type No. 12215/0, equipped with a wide range goniometer type No. 42273/0, copper tube type No. 32147, proportional counter type No. 57250/1; all coupled to the Norelco circuit panel type No. 12206/53. The copper K alpha radiation is supplied by operating the tube at a constant potential of 40 kilovolts and a current of 35 milliamperes. A nickel filter is used to remove K beta radiation. The detector voltage is 1660 volts and the pulse height analyzer is set to accept pulses with amplitudes between 10 and 30 volts only. Slits used are divergence 1°, receiving 0.006 inches and scatter 1°. Strip chart recordings for identification are made with a scanning speed of 1° per minute, time and constant of 1 second and a full scale at $10^3$ counts per second. No correction is made for Kα doublet or instrumental broadening of the band widths.

Suitable catalyst according to this invention are magnesium chromite having X-ray diffraction peaks within the d-spacings 4.80–4.82; 2.94–2.96; 2.50–2.52;

2.40–2.42; 2.07–2.09; 1.90–1.92; 1.69–1.71; 1.59–1.61, 1.46–1.48; 1.40–1.42, and the most intense peaks being between 2.50–2.52.

Chromite formation can be accomplished by reacting an active compound of chromium with an active compound of magnesium. By active compound is meant a compound which is reactive under the conditions to form the chromite. Starting compounds of chromium and magnesium may be such as the nitrates, hydroxides, hydrates, oxalates, carbonates, acetates, formates, halides, oxides, etc.

The catalyst may contain an excess of chromium over the stoichiometric amount, which is 2 atoms of chromium per atom of Mg,(MgCr$_2$O$_4$). There may be from 10 to 200 percent excess of the chromium. Similarly, the Mg portion of the chromite may be present in more than a stoichiometric amount.

The magnesium chromite can be prepared by precipitation, dry or wet milling or mixing, by precipitation of one of the ingredients in the presence of the other, coprecipitation and impregnation of one or more of the solid ingredients with aqueous or non-aqueous solutions of salt of the ingredients.

One particularly useful method of preparing the magnesium chromites has been by coprecipitation from an aqueous solution. Soluble metal salts of chromium and magnesium component as described above are dissolved in water and an insoluble precipitate formed by the use of a precipitating agent.

Soluble metal salts are known for essentially all metals. In specific regard to the metal components of the present invention the following soluble metal compounds are illustrative: chromium (III) nitrate, magnesium chloride and aluminum sulfate. The precipitating agent is one which, when reacted with the appropriate metal ion or mixtures of ions in solution, forms an insoluble compound which can be converted to the chromite. The alkali and alkaline earth hydroxides such as NaOH, KOH, CaOH, as well as ammonium hydroxide cause the precipitation of the metal hydroxides which are converted on heating to the chromites. After the precipitate is washed and dried it is calcined to form the chromite.

The formation of the chromite is obtained by heating the precipitates or other intimate mixture of chromite precursors at an elevated temperature, e.g., 400°–1100° C (generally no greater than 1300° C), in a controlled atmosphere, i.e., air, nitrogen, helium, a reducing atmosphere such as hydrogen, carbon monoxide or the like, for a sufficient time, i.e., usually 5 minutes to 4 hours. A calcination temperature of 550°–800° C has been found particularly useful and temperatures in the range of 600°–750° C. have been found to produce excellent catalysts. Catalysts prepared at 900°–1100° C have also been found to be highly desirable.

The aluminum component of the catalyst, if any, may be added prior to and/or after the calcination and formation of the chromite. The aluminum component is conveniently added to the chromite as a soluble salt in a slurry with the chromite after which it is dried, then decomposed by heating to aluminum oxide. Alternatively, insoluble aluminum oxide, hydroxide or oxyhydroxide can be added to the magnesium chromite, preferably in a highly divided state. Yet another desirable way to place the aluminum in the catalyst is by coprecipitation of aluminum hydroxide with the Me hydroxide and chromium hydroxide.

The aluminum will be present in the catalyst in all forms in an atomic ratio of Al:Cr of 0.0004 to 1.2:1. For example, in terms of a soluble aluminum compound such as aluminum sulfate added to the magnesium chromate; this would represent from about 0.1 to 75 weight percent Al$_2$(SO$_4$)$_3$.16H$_2$O based on the total weight of the catalyst. A more preferred range of Al:Cr atom ratio is 0.04 to 0.8:1. Generally the higher weight percentages of aluminum compound, i.e., 50 weight percent or more, are applied to the magnesium chromites having high surface areas, e.g., 50m$^2$ per gram or more.

The promoter selected from the group consisting of B, Si, Sn, Pb, and Se may be added to either the preformed MgCr$_2$O$_4$ or to the precursor thereof. The same techniques described above for incorporating Al into the chromites may be used to incorporate these promoters. It has not been determined whether any of the promoter is incorporated into the crystalline structure of the chromite or if incorporated, how much. Insofar as the present invention is concerned, this aspect of the mechanism is not essential to the operation of the invention. It is summized that a portion of the promoter may be incorporated into the crystalline structure of the MgCr$_2$O$_4$; however, a larger amount of the promoter is probably also present as the uncombined oxide. These views of the possible combined nature of the promoter and magnesium chromite are not intended to limit the scope of the invention.

The active catalysts can be pelleted or applied to a suitable support such as alumina, silica gel, silica-alumina, firebrick, kieselguhr, quartz and the like. The catalyst is the active surface available for contact with the gaseous reactants.

The catalysts of this invention can be applied to the dehydrogenation of a wide variety of organic compounds. Such compounds normally will contain from 2 to 20 carbon atoms, at least one

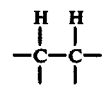

grouping, having a boiling point below about 350° C., and may contain other elements in addition to carbon and hydrogen such as oxygen, halogens, nitrogen and sulfur. Preferred are compounds having 2 to 12 carbon atoms, and especially preferred are compounds of 3 to 5 carbon atoms.

Representative materials which are dehydrogenated by the novel process of this invention include n-butane, methyl butane, methyl butenes, ethyl toluene, alkyl chlorobenzenes, ethyl benzene, ethyl naphthalene, isobutyronitrile, propyl chloride, isobutyl chloride, ethyl fluoride, ethyl bromide, n-pentyl iodide, ethyl dichloride, 1,3-dichlorobutane, 1,4-dichlorobutane, the chlorofluroethanes, methyl pentanes, methylethyl ketone, diethyl ketone, n-butyl alcohol, methyl propionate, and the like.

Among the types of organic compounds which may be dehydrogenated by means of the process of this invention are nitriles, amines, alkyl halides, ethers, esters, aldehydes, ketones, alcohols, acids, alkyl aromatic compounds alkyl heterocyclic compounds, cycloalkanes, alkanes, alkenes and the like.

Suitable dehydrogenation reactions are the following: acyclic compounds having 4 to 5 non-quaternary contiguous carbon atoms to the corresponding olefins, diolefins or acetylenes having the same number of carbon atoms; aliphatic hydrocarbons having 6 to 16 carbon atoms and at least one quaternary carbon atom to aromatic compounds, such as 2,4,4-trimethylpentene-1 to a mixture of xylenes; acyclic compounds having 6 to 16 carbon atoms and no quaternary carbon atoms to aromatic compounds such as n-hexenes to benzene; cycloparaffins and cycloolefins having 5 to 8 carbon atoms to the corresponding olefin, diolefin or aromatic compound, e.g., cyclohexane to cyclohexene or cyclohexadiene or benzene; aromatic compounds having 8 to 12 carbon atoms including one or two alkyl side chains of 2 to 3 carbon atoms to the corresponding aromatic with unsaturated side chain such as ethyl benzene to styrene.

Illustration of dehydrogenations include butane to butenes and butadiene; propionitrile to acrylonitrile; propionaldehyde to acrolein; ethyl chloride to vinyl chloride; methyl isobutyrate to methyl methacylate; 2 or 3-chlorobutene-1 or 2,3-dichlorobutane to chloroprene; ethyl pyridine to vinyl pyridine; ethylbenzene to styrene; isopropylbenzene to $\alpha$-methyl styrene; ethylchlorohexane to styrene; cyclohexane to benzene; ethane to ethylene to acetylene; propane to propylene or methyl acetylene, allene, or benzene; isobutane to isobutylene; n-butane to butene and butadiene-1,3; n-butene to butadiene-1,3 and vinyl acetylene; methyl butenes to isoprene; cyclopentane to cyclopentene and cyclopentadiene-1,3; n-octane to ethyl banzene and ortho-xylene; monomethylheptanes to xylenes; ethyl acetate to vinyl acetate; 2,4,4-trimethylpentane to xylenes; and the like.

The preferred compounds to be dehydrogenated are hydrocarbons with a particularly preferred class being acyclic non-quaternary hydrocarbons having 3 to 5 carbon atoms or ethyl benzene and the preferred products are propene, n-butene-1 or 2, butadiene-1,3, vinyl acetylene, 2-methyl-1-butene, 3-methyl-1-butene, 3-methyl-2-butene, isoprene, styrene or mixtures thereof. Especially preferred as feed are n-butene-1 or 2 and the methyl butenes and mixtures thereof such as hydrocarbon mixtures containing these compounds in at least 50 mol percent.

The dehydrogenation reaction may be carried out at atmospheric pressure, superatmospheric pressure or at sub-atmospheric pressure. The total pressure of the system will normally be about atmospheric pressure or sub-atmospheric pressure. Generally the total pressure will be between about 1 p.s.i.a. and about 75 p.s.i.a. Preferably the total pressure will be less than about 50 p.s.i.a.

The temperature of the dehydrogenation reaction will generally be in a range of about 350° to 700° C with excellent results being obtained in the range of 400° to 650° C. The gaseous reactants can be conducted through the reaction chamber at a fairly wide range of flow rates. The optimum flow rates will be dependent upon such variables as the temperature of reaction, pressure, particle size of the catalyst, and so forth. Desirable flow rates may be established by one skilled in the art. Generally the flow rates will be within the range of about 0.10 to 10 liquid volumes of the organic compound to be dehydrogenated per volume of dehydrogenation zone containing catalyst per hour (referred to as LHSV). Usually the LHSV will be between 0.15 and about 5. For calculation, the volume of a fixed bed dehydrogenation zone containing catalyst is that original void volume of reactor space containing catalyst.

The dehydrogenation is carried out in a series of cycles which comprise dehydrogenation of a suitable feed over the catalysts of the invention under the conditions as defined for a period of time, usually about 6 to 12 minutes followed by a regeneration cycle during which the coke deposited from the dehydrogenation is burnt off. The regeneration can be longer or shorter than the dehydrogenation cycle as needed to remove the coke, usually about 6 to 12 minutes will be sufficient. The coke is removed by passing oxygen at a temperature of 550° to 650° C. over the catalyst. A convenient source of oxygen is air, however, pure oxygen or a mixture of oxygen with inert gases, such as nitrogen, either in the same or different proportions as air, can be used.

The following Examples which are submitted to demonstrate the operation of the invention are carried out at atmospheric pressure, i.e., about 15 p.s.i.a. The presence of the chromite structure was established for the catalysts by X-ray analysis as described previously. In the Examples percents are by weight except that results are given as mole percents. Analysis of the products was by gas-liquid chromatography.

Isothermal Atmospheric Reactor

The reactor was a 29 × 3/4 inch Vycor tube equipped with a heating mantle and appropriate equipment. A 40 cc bed of catalyst was placed in the reactor and reactant feed (or regenerative air) added at the bottom of the reactor with product coming off overhead. The catalyst was heated to the reaction temperature in a nitrogen atmosphere. The process was carried out automatically with a make cycle (dehydrogenation) of 9 minutes and 9 minutes regeneration and repeat of the cycle. This gave a total cycle time of 18 minutes. When desired, the partial pressure of the n-butane during the reaction cycle was reduced below atmospheric by dilution with nitrogen. The total effluent from either or both cycles was collected in an inflatable collecting device and analyzed by gas chromatography. Alternately, the effluent from the regeneration cycle was passed through calibrated infrared analyzer to determine the amount of $CO_2$ produced during regeneration (coke burn-off). By either method of analysis the amount of coke deposited on a catalyst during the reaction cycle was determined and could be taken into account when calculating the overall activity and selectivity of a catalyst. The temperatures were controlled by a thermoelectric temperature controller and recorded on a Leeds and Northrup 24-point recorder.

EXAMPLES 1-3

Catalyst Preparation

1. $MgCr_2O_4$ no promoter

Reagents

1. Magnesium carbonate (Marinco CL, Merck Chem. Div., Merck & Co., Inc., Rahway, N.J., Assay as MgO = 43.0%).
2. Hydrous chromium (III) oxide; Assay as $Cr_2O_3$ = 55.3%
3. Baker analyzed reagent magnesium chloride, assay as $MgCl_2.6H_2O = 99.8\%$.

44.5 gms. of reagent (1), 137.4 gms. of reagent (2) and 5.1 gms. of reagent (3) were slurried together for about 10 minutes in a 1 qt. Waring blender using ~ 300 mls. of demineralized water as the slurrying medium. The slurry was dried overnight at ~ 120° C. The dried slurry was crushed to sub 40 mesh particles and calcined to 800° C in an atmosphere of $N_2$.

2. $MgCr_2O_4$ + 0.05 mol Se

Same as procedure 1 above except that the slurry medium was composed of 3.34 gms. of Fisher Scientific Certified Selenous Acid, (Assay as $H_2SeO_3$ = 96.4%) dissolved in ~ 300 mls. of demineralized water.

3. $MgCr_2O_4$ + 0.05 mol Pb

Same as procedure 1 above except that the slurry medium was composed of 6.97 gms. of Baker Analyzed reagent lead chloride (Assay as $PbCl_2$ = 99.8%) dissolved in ~ 400 mols. of demineralized water. To this solution was added, dropwise and with good mixing, conc. aq. ammonia to a final pH of ~ 7.0.

Samples of each catalyst were prepared for testing by being deposited as 50% actives on AMC support. Additional test samples were prepared by combining 30 weight % $Al_2(SO_4)_3.16H_2O$ with the $MgCr_2O_4$ and depositing as 45% actives on AMC support.

The samples were tested as described above and the results are set out in TABLE I.

EXAMPLES 4-6

Catalyst Preparation

Variable amounts of promoter

4. $MgCr_2O_4$ + Si

The following procedure for preparing catalysts was as follows:

Tetraethylorthosilicate (Ethyl Silicate, pure, Union Carbide Chem. Co., Div. of Union Carbide, N.Y., 17, N.Y.) was added to a solution of 250 cc of demineralized water and 50 cc of ethanol. This mixture was stirred vigorously and 0.75 cc of conc. HCl added dropwise. Stirring was continued while the orthosilicate was hydrolyzed - the reaction being conducted at room temperature. (Nearly all of the ethyl silicate was hydrolyzed within about 15 minutes). After hydrolysis was complete, the solution was transferred to a 1 qt. Waring blender. To the blender was added 137.4 gms. of hydrous Cr (III) oxide, (Assay as $Cr_2O_3$=55.3), 44.5 gms. of magnesium carbonate (Marinco CL, Merck Chem. Div., Merck & Co., Inc., Rahway, N.J., Assay as MgO = 43.0%), and 5.1 gms. of magnesium chloride (Baker analyzed reagent, Assay as $MgCl_2.6H_2O$ = 99.8%). The mixture was blended for about 10 minutes, dried overnight in an oven at ~ 120° C, crushed to sub 20 mesh particles and calcined in $N_2$ to 800° C.

TABLE I

| | | | RESULTS* | | | | | | | | | |
|---|---|---|---|---|---|---|---|---|---|---|---|---|
| PROMOTER | | | | | | | 30 Wt.%$Al_2(SO_4)_3.16H_2O$ | | | | | |
| Example | Type | Mol | C | S | | Y | | C | S | | Y | |
| | | | | Bu | Bd | Bu | Bd | | Bu | Bd | Bu | Bd |
| 1 | O | 0 | 33.5 | 63.0 | 10.4 | 21.1 | 3.5 | 67.9 | 75.2 | 8.5 | 51.1 | 5.8 |
| 2 | Se | 0.05 | 39.3 | 66.2 | 13.6 | 26.0 | 5.3 | 59.6 | 76.9 | 10.2 | 45.9 | 6.1 |
| 3 | Pb | 0.05 | 51.2 | 70.2 | 15.8 | 35.9 | 8.1 | 58.1 | 74.8 | 15.7 | 43.4 | 9.1 |

*Mol % C = Conversion, S = Selectivity, Y = Yield, Y = C × S, Bu = Butenes, Bd = Butadiene The amount of ethyl silicate used in the preparation was as follows:

| Preparation No. | Amount of ethyl silicate used in the preparation (gms.) |
|---|---|
| 4A | 4.17 |
| 4B | 5.21 |
| 4C | 6.25 |

| Preparation No. | Amount of ethyl silicate used in the preparation (gms.) |
|---|---|
| 4D | 7.29 |

5. $MgCr_2O_4$ + Sn

Stannous chloride (Baker analyzed reagent, Assay as $SnCl_2.2H_2O$ = 98.0%) dissolved in 250 cc of demineralized water acidified with enough conc. HCl (~ 1 cc) to yield a clear solution. To this solution was added dropwise and with good stirring, conc. aq. ammonia to a final pH of > 7.0 (7.1 - 7.2). This solution was transferred to a 1 qt. Waring blender. To the blender was added 137.4 gms. of hydrous Cr (III) oxide, (Assay as $Cr_2O_3$ = 55.3), 44.5 gms. of magnesium carbonate (Marinco CL, Merck Chem. Div., Merck & Co., Inc. Rahway, N.J., Assay as MgO = 43.0%), and 5.1 gms. of $MgCl_2.6H_2O$ (Baker analyzed reagent, Assay as $MgCl_2.6H_2O$ = 99.8%). Additional demineralized water was added as needed to yield an easily slurried mixture. The mixture was slurried for ~ 10 minutes, dried overnight ~ 120° C, crushed to sub 40 mesh particles and calcined in $N_2$ to 800° C.

The amount of stannous chloride (see above) used in each preparation is given below:

| Preparation No. | Amount of stannous chloride used in the preparation (gms.) |
|---|---|
| 5A | 4.60 |
| 5B | 5.76 |
| 5C | 6.91 |
| 5D | 8.06 |

6. $MgCr_2O_4$ + B

Boric acid (Baker analyzed reagent, Assay as $H_3BO_3$ = 99.7%) was dissolved in 250 mls. of demineralized water and this solution transferred to a 1 qt. Waring blender. To the blender was then added 137.4 gms. of hydrous Cr (III) oxide, (Assay as $Cr_2O_3$ = 55.3) 44.5 gms. of magnesium carbonate (Marinco CL, Merck Chem. Div., Merck & Co., Inc., Rahway, N.J., Assay as MgO = 43.0%) and 5.1 gms. of $MgCl_2.6H_2O$ (Baker analyzed reagent, Assay as $MgCl_2.6H_2O$ = 99.8%). Additional demineralized water was used as needed to yield an easily slurried mixture. The mixture was slurried for ~ 10 minutes, dried overnight in an oven at ~ 120° C, crushed to sub 40 mesh particles and calcined in $N_2$ to 800° C.

The amount of boric acid used in each preparation is given below:

| Preparation No. | Amount of boric acid used in the preparation (gms.) |
|---|---|
| 6A | 1.24 |
| 6B | 1.55 |
| 6C | 1.86 |
| 6D | 2.17 |

Each catalyst prepared above was deposited on AMC support (45% actives). The tin promoted compositions were also modified with 30 weight % $Al_2(SO_4)_3.16H_2O$ and deposited as 45% actives on AMC. The catalyst compositions were tested as described above. The results of testing are set out below in TABLE II.

TABLE II
RESULTS

| | PROMOTER | | | | | | | 30 Wt.%$Al_2(SO_4)_3 . 16H_2O$ | | | | |
|---|---|---|---|---|---|---|---|---|---|---|---|---|
| Example | Type | Mol | C | S | | Y | | C | S | | Y | |
| | | | | Bu | Bd | Bu | Bd | | Bu | Bd | Bu | Bd |
| 4 | A | Si | 0.04 | 53.6 | 69.6 | 11.7 | 37.3 | 6.3 | | | | |
| | B | Si | 0.05 | 55.2 | 71.2 | 11.3 | 39.3 | 6.3 | | | | |
| | C | Si | 0.06 | 59.0 | 68.9 | 13.4 | 40.7 | 7.9 | | | | |
| | D | Si | 0.07 | 57.5 | 69.9 | 13.0 | 40.2 | 7.5 | | | | |
| 5 | A | Sn | 0.04 | 40.3 | 66.3 | 13.0 | 26.8 | 5.2 | 63.6 | 72.9 | 14.3 | 46.4 | 9.1 |
| | B | Sn | 0.05 | 45.1 | 68.9 | 14.9 | 31.1 | 6.7 | 64.8 | 72.6 | 14.3 | 47.0 | 9.3 |
| | C | Sn | 0.06 | 41.4 | 65.7 | 14.1 | 27.2 | 5.8 | 62.8 | 72.9 | 13.7 | 45.8 | 8.6 |
| | D | Sn | 0.07 | 42.2 | 66.5 | 14.6 | 28.1 | 6.2 | 62.5 | 73.4 | 14.0 | 45.9 | 8.8 |
| 6 | A | B | 0.04 | 45.3 | 66.2 | 14.5 | 30.0 | 6.6 | | | | |
| | B | B | 0.05 | 47.0 | 72.3 | 12.2 | 33.9 | 5.7 | | | | |
| | C | B | 0.06 | 45.8 | 68.9 | 12.6 | 31.6 | 5.8 | | | | |
| | D | B | 0.07 | 45.9 | 69.3 | 14.3 | 31.8 | 6.6 | | | | |

The invention claimed is:

1. A dehydrogenation catalyst consisting essentially of (1) magnesium chromite + selenium oxide, (2) magnesium chromite + selenium oxide + aluminum oxide, or (3) $MgAl_xCr_{2-x}O_4$ selenium oxide wherein the ratio of Al:Cr is from 0.0004 to 1.2:1 and x is a number of from more than 0 up to less than 1.

2. The catalyst according to claim 1 wherein a promoting amount is from 0.001 to 0.25 mol of selenium per mol of magnesium chromite.

3. The catalyst according to claim 2 wherein a promoting amount is from 0.03 to 0.08 mol of selenium per mol of magnesium chromite.

* * * * *